(12) United States Patent
Okada

(10) Patent No.: US 6,476,852 B1
(45) Date of Patent: Nov. 5, 2002

(54) IMAGING DEVICE FOR ENDOSCOPE EQUIPPED WITH BOTH NTSC SYSTEM AND PAL SYSTEM

(75) Inventor: Fujio Okada, Omiya (JP)

(73) Assignee: Fuji Photo Optical Co., Ltd., Saitama (JP)

(*) Notice: Subject to any disclaimer, the term of this patent is extended or adjusted under 35 U.S.C. 154(b) by 0 days.

(21) Appl. No.: 09/340,050

(22) Filed: Jun. 28, 1999

(30) Foreign Application Priority Data

Jul. 10, 1998 (JP) .......................................... 10-195463

(51) Int. Cl.⁷ ................................................ H04N 9/47
(52) U.S. Cl. ........................................ 348/65; 348/445
(58) Field of Search .............................. 348/65, 68, 76, 348/71, 46, 77, 66, 441, 445, 443, 447, 454, 458, 459, 558; 345/154; 382/128, 266; 600/109; H04N 7/18, 7/01

(56) References Cited

U.S. PATENT DOCUMENTS

| | | | | |
|---|---|---|---|---|
| 5,282,020 A | * | 1/1994 | Tanaka ........................ | 348/441 |
| 5,450,129 A | * | 9/1995 | Matoba et al. ............... | 348/445 |
| 5,726,715 A | * | 3/1998 | Endress ....................... | 348/565 |
| 6,154,248 A | * | 11/2000 | Ozawa et al. ................. | 348/65 |

FOREIGN PATENT DOCUMENTS

| | | |
|---|---|---|
| JP | 60-243625 | 12/1985 |
| WO | WO 92/20187 | 11/1992 |

OTHER PUBLICATIONS

Japanese Patent Office, "Patent Abstracts of Japan," Publication No.: JP 0007298202 AA, Publication Date: Nov. 10, 1995, Application No.: 1994 83292, Application Filing Date: Apr. 21, 1994.

Japanese Patent Office, "Patent Abstracts of Japan," Publication No.: JP 0005191819 AA, Publication Date: Jul. 30, 1993, Application No.: 1991 140341, Application Filing Date: Jun. 12, 1991.

* cited by examiner

Primary Examiner—Chris Kelley
Assistant Examiner—Gims Philippe
(74) Attorney, Agent, or Firm—Snider & Associates; Ronald R. Snider

(57) ABSTRACT

An imaging device for an endoscope which can restrain the flicker of a screen caused when converting the television system, and furthermore, which makes it possible to unify processor circuits performing the processing of different systems. Having an NTSC system oscillator and a PAL oscillator with an oscillating frequency of $N \cdot f_{h2}$, and a switching device for selecting them in a scope equipped with a CCD suitable for the number of scanning lines, for example, of the NTSC system, and it drives the CCD on the basis of a timing signal formed in each of the selected oscillators. That is, when the PAL system is selected, the picture data is taken out from the CCD by a horizontal synchronization signal with a frequency of 15.625 kHz ($f_{h2}$), and in a memory section on the processor side, write-in and read-out of the picture data are also performed by a horizontal synchronization signal with this frequency $f_{h2}$, and therefore, difference between the write-in speed and the read-out speed becomes small, and the flicker of a screen is restrained.

3 Claims, 4 Drawing Sheets

IMAGING DEVICE FOR ENDOSCOPE EQUIPPED WITH BOTH NTSC SYSTEM AND PAL SYSTEM

BACKGROUND OF THE INVENTION

This application claims the priority of Japanese Patent Application No. 10-195463 filed on Jul. 10, 1998 which is incorporated herein by reference.

1. Field of the Invention

The present invention relates to an imaging device for an endoscope, and more particularly, it relates to the composition of an endoscope system which can display a picture imaged by using one scope, by either system selected from the NTSC system and the PAL system.

2. Description of the Prior Art

In FIG. 3, one example of the composition of a conventional electronic endoscope is shown, and as shown in the figure, for example, on the scope side, a timing generator 2 is connected to a CCD 1 which is a solid imaging element. To this timing generator 2, a crystal oscillator 3 for the NTSC (television) system is connected, and various types of drive signals with specified frequencies are formed by using, for example, a signal with a frequency of about 14.32 MHz oscillated in this oscillator 3, and this is given to the CCD 1.

To the CCD 1, an AGC (automatic gain control) circuit including a CDS (correlative double sampling) circuit is connected, and to this AGC circuit 5, a DSP (digital signal processor) 7 is connected through an A/D converter 6. Then, a first CPU 8 for controlling these circuits is provided.

On the other hand, on the side of the PAL processor to which the scope is connected, at the position where the signal outputted from the DSP 7 is inputted, a memory section 10 equipped with an imaging memory 10A and a display memory 10B is provided, and to the rear stage of this memory section 10, a D/A converter 11 is connected.

Furthermore, a second CPU 12 for controlling these circuits, a PAL system oscillator 13 for outputting, for example, an oscillating signal with a frequency of about 17.73 MHz, and a ROM 14 (read only memory) are provided, and a synchronization signal formed on the basis of the PAL oscillating signal is given to the memory 10. Furthermore, in the ROM 14, the information to make the scope side (the first CPU 8) recognize that the processor is a PAL system processor is stored.

According to an electronic endoscope composed like this, when an oscillating signal with a frequency of about 14.32 MHz is inputted into the timing generator 2 from the oscillator 3 of the NTSC system, a horizontal synchronization signal fh1 with a frequency of 15.734 kHz vertical synchronization signal $f_{v1}$ with a frequency of 59.94, Hz, a horizontal CCD drive pulse and a vertical pulse are formed from the oscillating signal in this generator 2, and these are outputted to the CCD 1.

In this CCD 1, a picture signal is read out on the basis of each of the synchronization signals, and this picture signal is converted into a digital signal to be supplied to the DSP 7 after specified amplification, sample hold, and the like have been performed in the CDS/AGC 5. In this DSP 7, gamma processing and the like are performed, and the output of this DSP 7 is sent to the memory section 10 on the processor side.

In this memory section 10, the picture signal is once written in the imaging memory 10A in the timing of the NTSC system, but when reading out the signal, the signal is read out on the basis of the PAL system synchronization signal, that is, a horizontal synchronization signal $f_{h2}$ with a frequency of 15.625 kHz and a vertical synchronization signal $f_{v2}$ with a frequency of 50 Hz, and this picture signal is stored in the display memory 10B. Accordingly, while shifting from the imaging memory 10A to the display memory 10B, the conversion to the PAL picture data is performed. By the way, the horizontal synchronization signal $f_{h2}$ and the vertical synchronization signal $f_{v2}$ are formed by the second CPU 12 from the output of the oscillator 13.

After that, the picture signal read out from the display memory 10B is converted into an analog signal at the D/A converter 11, and this signal is outputted to a PAL monitor through a specified processing circuit, and a picture in an observed object is displayed on the PAL monitor. By the way, in the case where a picture is displayed by the NTSC system, an NTSC system processor is connected to the scope.

However, in an electronic endoscope system of converting from the NTSC system to the PAL system, the frequencies of the synchronization signals are different as mentioned above, and therefore, there is such a problem that the conversion screen flickers especially in the case where the observed object moves. This is caused by the reason that there is a difference between the write-in speed and the read-out speed to the imaging memory 10A of the memory section 10 and the write-in speed depends on the horizontal synchronization signal and the vertical synchronization signal of the NTSC system and the read-out speed depends on the horizontal synchronization signal and the vertical synchronization signal of the PAL system.

In FIG. 4, the difference between the picture display processing of the NTSC system and the picture display processing of the PAL system is shown, and the number of scanning lines is 525 in the NTSC system but in the meantime, the number is 625 in the PAL system, and furthermore, the cycle of the horizontal synchronization signal is 15.734 kHz in the NTSC system but the cycle is 15.625 kHz in the PAL system, and consequently, there is a difference of $t1=1/(15.625\times10^3) -1/(15.734\times10^3)$. Accordingly, in the data of 1 field (or 1 frame), the write-in speed in the NTSC system is faster than the read-out speed in the PAL system, and in the course of 1 field, the data of the next field with a time difference is mixed, and eventually, a flicker of the screen is caused in the picture with movement or the like.

Furthermore, the PAL system processor described in FIG. 3 is produced separately from the NTSC system processor, and consideration for the difference of the power source or the like is also necessary, but it is a convenience if at least the signal processing processor section can be one circuit composition regardless of the difference of the system.

BRIEF SUMMARY OF THE INVENTION

The present invention is made due to the above problems, and it is an object thereof to provide an imaging device for an endoscope equipped with both the NTSC system and the PAL system in which it is possible to restrain the flicker of the screen caused when converting the television system, and further, in which it is possible to unify the processor circuit for performing the display processing of different systems.

In order to attain the above object, the present invention comprises: a scope for capturing an observed object; an imaging element suitable for the number of scanning lines of either the NTSC system or the PAL system for imaging the picture of the observed object; an oscillator for the NTSC system and an oscillator for the PAL system; a drive means which selects either of both the oscillators and drives the imaging element on the basis of the timing signal corresponding to each selected system; and a picture processing processor which processes the picture signal outputted from the imaging element to selectively form a picture of the NTSC system and a picture of the PAL system.

In the picture memory arranged in the picture processing processor, the frequency of the horizontal synchronization signal when writing in the picture signal obtained in the imaging element and the frequency of the horizontal synchronization signal when reading out the picture signal are conformed.

Furthermore, the PAL oscillator can be an oscillator to generate a frequency of N times about 15.625 kHz near the frequency of the horizontal synchronization signal for the NTSC.

Moreover, it is preferable to arrange the oscillator for the NTSC system and the oscillator for the PAL system in the scope when the imaging element is arranged in the scope and to arrange them onto the mounting member of the imaging element when the imaging element is connected to the eyepiece portion of the scope.

According to the above composition, the oscillator for the NTSC system and the oscillator for the PAL system are selectively used on the scope side, and when the NTSC system is selected, the picture data is extracted from the imaging element by the horizontal synchronization signal with a frequency of 15.734 kHz. Usually, as this imaging element, a CCD having a number of horizontal lines suitable for the NTSC system is used, and on the processor side, the synchronization signal with the above frequency is also used, and therefore, in this case, the picture display processing is performed without question similarly to the previous processing.

On the other hand, when the PAL system is selected, the picture data is extracted from the CCD by the horizontal synchronization signal with a frequency of 15.625 kHz formed by the oscillator for the PAL system, and this picture data is stored in the memory on the processor side in the same timing. After that, from this memory, the picture data is read out by the horizontal synchronization signal with a frequency of the above PAL system, and at this moment, the conversion and expansion (compression) of the scanning line data for converting the number of scanning lines from 525 to 625 is performed.

According to this, the vertical synchronization term and the horizontal synchronization term in the write-in and the read-out to and from the memory (for conversion) are the same, and the time difference between the write-in and the read-out in 1 field (or 1 frame) becomes small, and the flicker of a screen is eliminated.

DETAILED DESCRIPTION OF THE PREFERRED EMBODIMENTS

Figure 1:
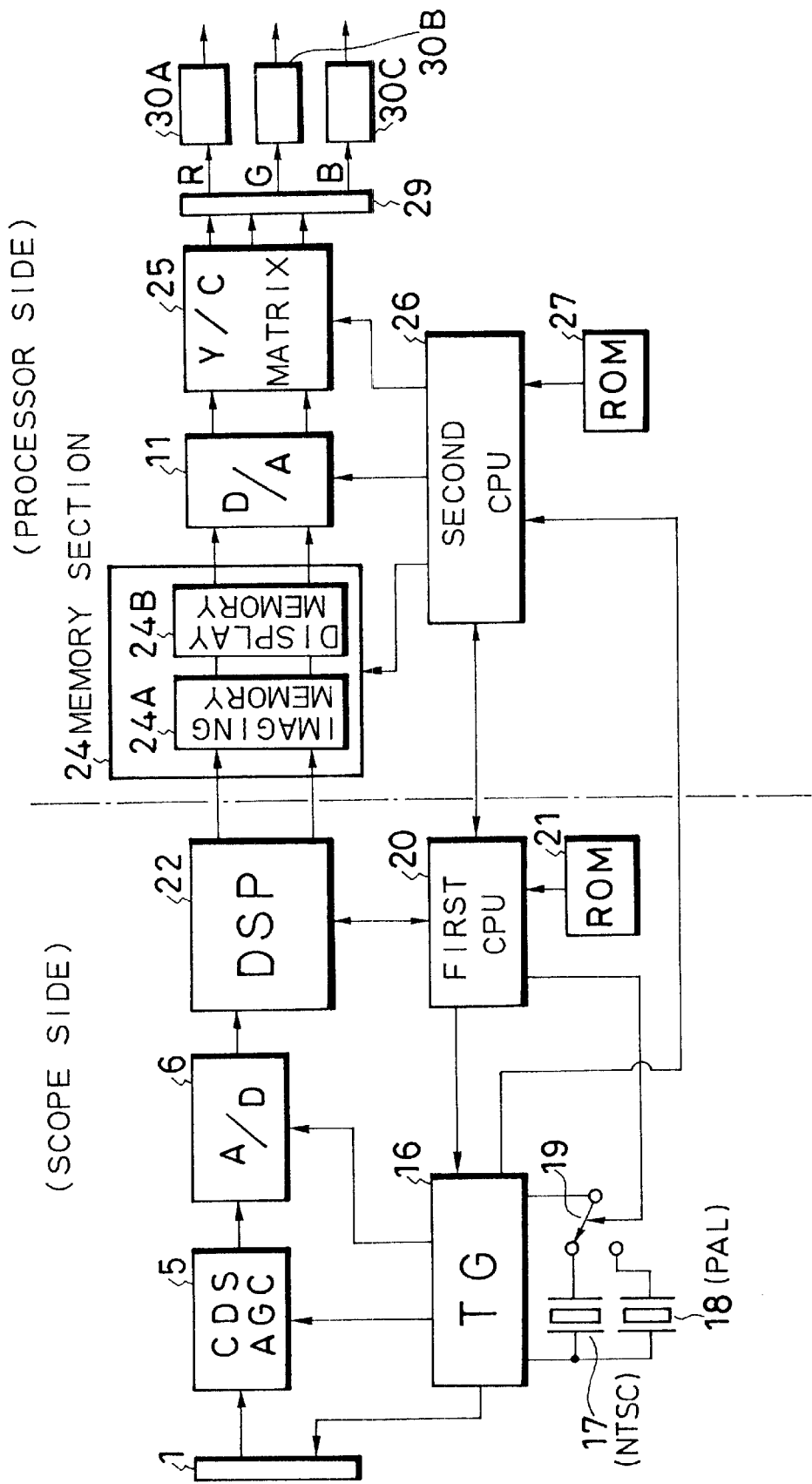
FIG. 1 is a block diagram showing the circuit configuration of an electronic endoscope equipped with both the NTSC system and the PAL system according to an embodiment of the present invention.
Figure 2:
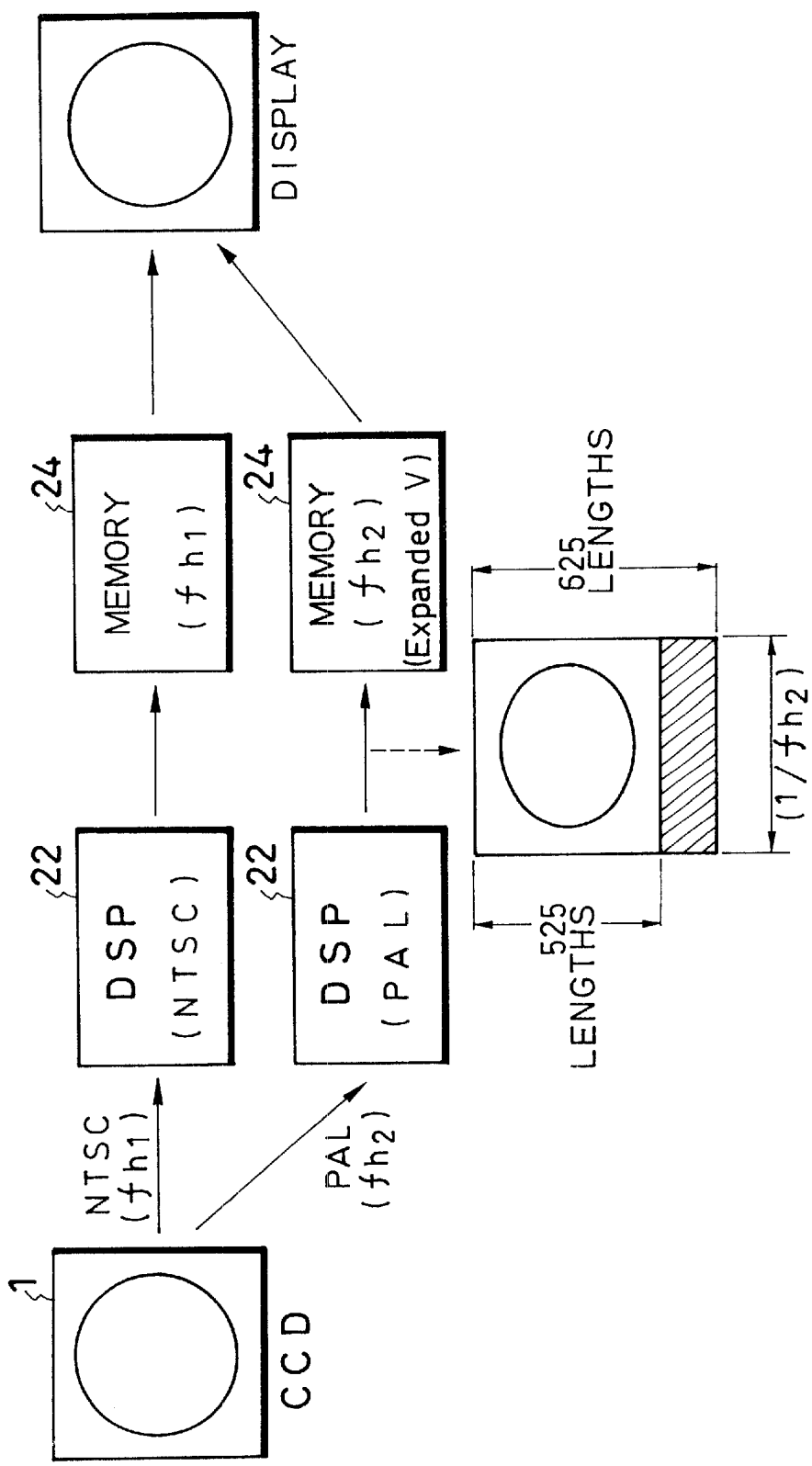
FIG. 2 is a schematic diagram of the picture data processing of the embodiment.
Figure 3:
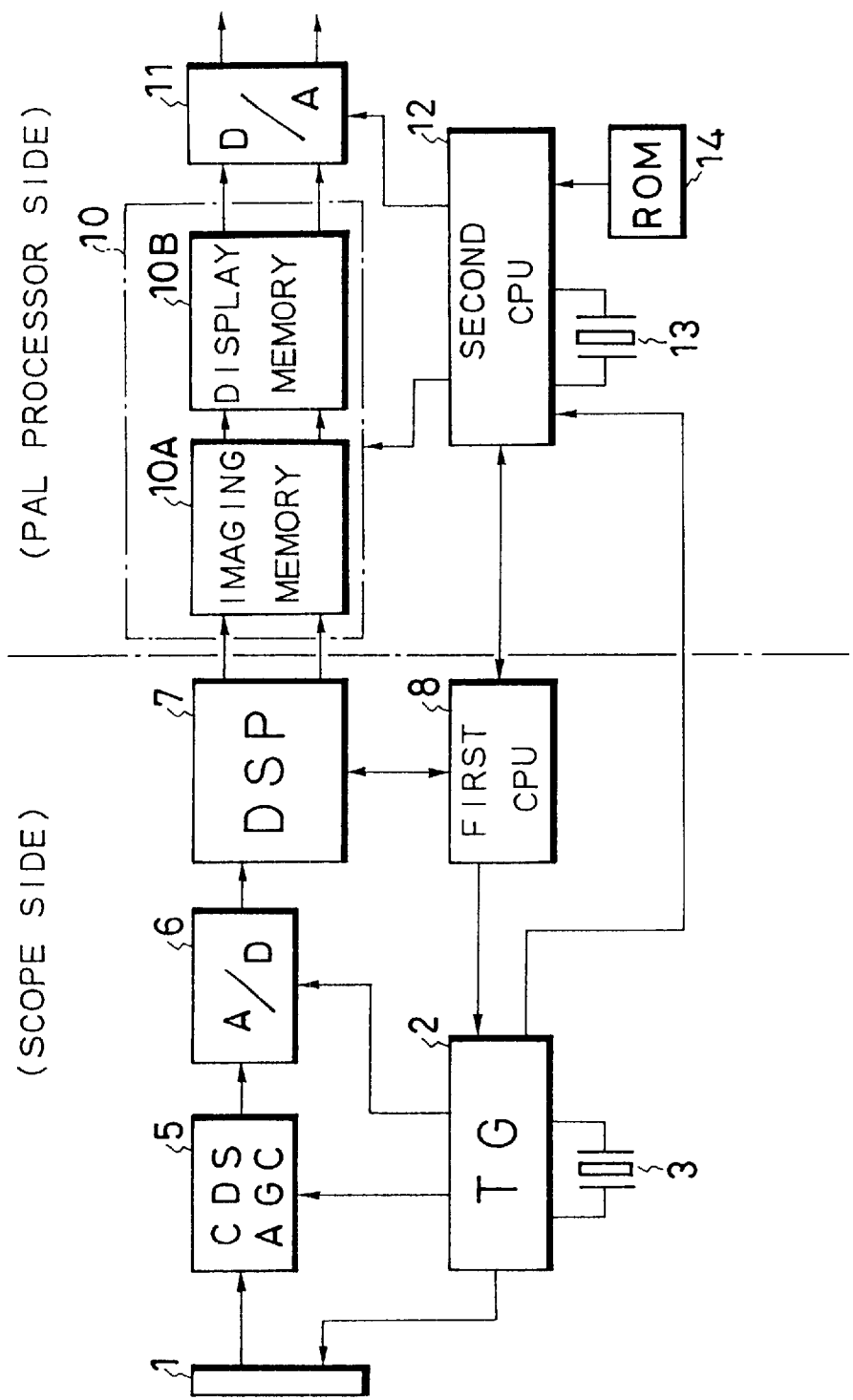
FIG. 3 is a block diagram showing the circuit composition of a conventional electronic endoscope.
Figure 4:
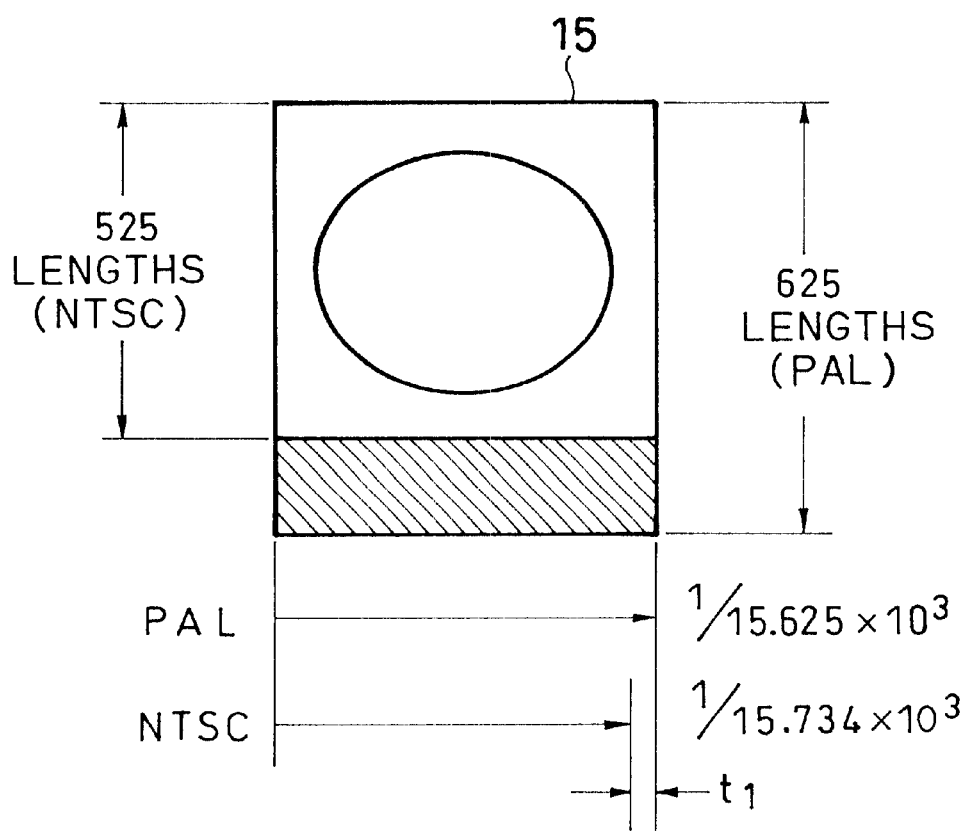
FIG. 4 is an explanation drawing showing the difference between an NTSC system and a PAL system in the prior art.

In FIG. 1 and FIG. 2, the circuit configuration of an electronic endoscope according to the embodiment is shown. In FIG. 1, the CCD 1 arranged on the scope side is an imaging element for the NTSC system having a number of scanning lines or the like suitable for the scanning line of the NTSC system, and to this CCD 1, a timing generator 16 is connected, and to this timing generator 16, an NTSC crystal oscillator 17, a PAL crystal oscillator 18, and a switching device 19 are provided. Furthermore, a first CPU 20 is provided, which controls the total while controlling this switching device 19, and by the control of this first CPU 20, either of the oscillators 17, 18 is selected.

The NTSC crystal oscillator 17 generates a signal with a frequency of about 14.32 MHz (N·$f_{h1}$), and the PAL oscillator 18 on the other side may be an oscillator which generates a signal with the above mentioned frequency of about 17.73 MHz, but in this example, an oscillator which generates a signal with a frequency of N·$f_{h2}$ [N times the frequency of the horizontal synchronization signal of 15.625 kHz (=$f_{h2}$)] near the NTSC oscillation frequency is used. Consequently, the change of the circuit member relating to the drive operation, the setting of a constant, or the like become easy. Moreover, to the first CPU 20, a ROM 21 storing setting data for the control meeting the NTSC system or the PAL system is connected.

Then, to the CCD 1, an AGC (automatic gain control) circuit including a CDS (correlative double sampling) circuit is connected similarly to that in the prior art, and to this AGC circuit 5, a DSP (digital signal processor) circuit 22 is connected through an A/D converter 6.

On the other hand, on the external processor side, a memory section 24 equipped with an imaging memory 24A and a display memory 24B, a D/A converter 11, a brightness/color signal (Y/C) matrix circuit 25, a second CPU 26 for controlling these circuits, and a ROM 27 storing the setting data for the control meeting the selected television system of the NTSC or the PAL are provided.

That is, the second CPU 26 gives the horizontal synchronization signal and the vertical synchronization signal with either a frequency of the NTSC system or a frequency of the PAL system to the memory section 24 according to the selected television system. Moreover, when the NTSC system is selected, the read-out of the data is performed without performing the conversion of the number of scanning lines, but when the PAL system is selected, the interpolated data is inserted into the horizontal line (number of scanning lines of 525) read out from the imaging memory 24A, and the expansion processing of the number of horizontal lines meeting the number of scanning lines of 625 is performed.

At the rear stage of the Y/C matrix circuit 25, buffers 30A, 30B, 30C are arranged for each of the color signals of R (red), G (green), and B (blue) through an isolation device 29, and to the rear stage of these buffers 30A to 30C, a monitor is connected.

A first example is configured like the above, and in the example, each television system can be selected by selective switches arranged at the processor or the like, and the state of selection of the switches can be grasped by the second CPU 26. Then, this second CPU 26 reads out the setting data of the selected system from the ROM 27 to set the processing contents of each circuit by this setting data. At the same time, the information of the selected system is also transmitted to the first CPU 20 on the scope side from this second CPU 26, and on this scope side, the selected setting data is read out from the ROM 21 by the first CPU 20 to set the processing contents of each circuit, and further, either of the above oscillators 17, 18 is selected and set.

That is, if the NTSC system is selected, the NTSC system oscillator 17 is connected to the timing generator 16 by the switching circuit 19. In this timing generator 16, the oscillating signal with, for example, a frequency of 14.32 MHz generated in the oscillator 17 is divided to form the horizontal synchronization signal with a frequency of 15.734 kHz ($f_{h1}$) and the vertical synchronization signal with a frequency of 59.94 Hz, and the driving pulse based on this is given to the CCD 1. Then, the picture signal extracted from this CCD 1 is subjected to the digital conversion after passing through the AGC circuit 5 for performing the correlative double sampling and the amplification processing, and as shown in FIG. 2, this digital picture signal is subjected to a specified processing by the DSP circuit 22, and it is supplied to the memory section 24 on the processor side.

In this memory section 24, the picture data is written in the imaging memory 24A in the timing of the synchronization signal formed in the timing generator 16, and after that, this picture data is read out in the same timing to be stored in the display memory 24B (as the data corresponding to the number of scanning lines of 525). The data of this display memory 24 is converted into the signals of R, G, and B from the brightness signal and the color difference signal in the Y/C matrix circuit 25 after being converted to the analog signal in the D/A converter 11. Then, each of these signals of R, G, and B is outputted to a monitor of the NTSC system through the isolation device 29 and the buffers 30 (A to C), and consequently, a picture of the NTSC system is displayed on the monitor.

On the other hand, when the PAL system is selected, the PAL system oscillator 18 is connected to the timing generator 16 by the switching circuit 19, and in this timing generator 16, the oscillating signal with, for example, a frequency of N·$f_{h2}$ generated in the oscillator 18 is divided to form the horizontal synchronization signal with a frequency of 15.625 kHz ($f_{h2}$) and the vertical synchronization signal with a frequency of 50 Hz, and the driving pulse based on this is given to the CCD 1. Accordingly, in case of this PAL system, the CCD 1 adjusted to the number of scanning lines of the NTSC system is driven in the timing of the synchronization signal of the PAL system.

After that, the picture signal obtained in this CCD 1 is supplied to the memory section 24 on the processor side through the AGC circuit 5 including the correlative double sampling processing and the DSP circuit 22 similarly to the above. In this memory section 24, the picture data is written in the imaging memory 24A in the timing of the synchronization signal of the PAL system formed in the timing generator 16, that is, by the horizontal synchronization signal with a frequency of 15.625 kHz.

Then, the data of this imaging memory 24A is read out in the same timing, and at the same time, it is subjected to the interpolation processing or the like, and eventually, as shown in FIG. 2, it is stored in the display memory 24B as the picture data (field or frame data) corresponding to the number of scanning lines of 625. The processing after this display memory 24B is similar to that in the case of the NTSC system, and this picture signal is outputted to a monitor of the PAL system through the buffers 30 (A to C), and as shown in FIG. 2, the same screen as in the case of the NTSC system is displayed.

According to the processing of the PAL system like this, the read-out and the write-in the imaging memory 24A of the memory section 24 are performed at a speed corresponding to the horizontal synchronization signal for the PAL, and therefore, the frequency of intermixture of data having a time difference because of the write-in of the data of the next field during the read-out of the data (passing) is less than that in the prior art, and the flicker of the screen is also eliminated.

Thus, in this example, it is possible to form and display both the picture data of the NTSC system and the picture data of the PAL system by using the CCD 1 for the NTSC system. Furthermore, in the above example, it is also possible to form and display the pictures of both systems by the processing similar to that of the above, by using a CCD 1 suitable for the scanning line of the PAL system, and furthermore, it is also possible to use a CCD for the PAL as an imaging element, and the scanning line change circuit in that case is made to perform the compression action.

Moreover, in the above example, a case where the device is applied to an electronic endoscope having the CCD arranged at the tip portion was described, but there is a device where the CCD is arranged at an eye piece portion of a fiber scope having an eye lens arranged to perform optical observation and an observed object seen through the fiber scope is formed as an electronic picture (for example, Japanese Patent Application Laid-Open No. 60-243625), and the present invention can also be applied to such an imaging device.

As mentioned above, according to the present invention, it is possible to restrain the flicker of a screen caused by the picture conversion to another television system, and further, it is possible to promote the unifying of the processor circuits performing the display processing of different television systems.

What is claimed is:

1. An imaging device for an endoscope equipped with both NTSC system and PAL system, comprising:

a scope for capturing an observed object;

an imaging element which images a picture of an observed object and which is suitable for either a number of scanning lines of NTSC system or a number of scanning lines of PAL system;

an oscillator for NTSC system and an oscillator for PAL system;

a drive means which selects either of both the oscillators and which drives said imaging element on the basis of a timing signal corresponding to each selected system; and a picture processing processor that comprises a memory for storing picture data which is timed according to the selected television system, so that a NTSC system picture and a PAL system picture are selectively formed;

wherein said PAL system oscillator is an oscillator which generates a frequency of N times about 15.625 kHz which is close to a frequency of a horizontal synchronization signal for said NTSC system;

wherein when said imaging element has a number of scanning lines for said NTSC system and when said PAL system is selected, said picture processing processor executes interpolation processing using the stored picture data which is read out from said memory, so that the picture data corresponding to the number of scanning lines of said PAL system is obtained.

2. The imaging device for an endoscope equipped with both NTSC system and PAL system according to claim 1, wherein in a picture memory arranged in said picture processing processor, a frequency of a horizontal synchronization signal when writing in a picture signal obtained by said imaging element and a frequency of a horizontal synchronization signal when reading out a picture signal are the same.

3. The imaging device for an endoscope equipped with both NTSC system and PAL system according to claim 1, wherein said oscillator for NTSC system and oscillator for PAL system are provided in a scope or on a member to which an imaging element is attached.

* * * * *